United States Patent
Olsson et al.

(10) Patent No.: US 8,029,725 B2
(45) Date of Patent: Oct. 4, 2011

(54) METHOD OF STERILIZING A PACKAGING MATERIAL BY MEANS OF A STERILIZATION AGENT CONTAINING HYDROGEN PEROXIDE

(75) Inventors: Håkan Olsson, Lomma (SE); Camilla Joscelyne, Södra Sandby (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 307 days.

(21) Appl. No.: 12/303,064

(22) PCT Filed: Apr. 4, 2007

(86) PCT No.: PCT/SE2007/000311
§ 371 (c)(1),
(2), (4) Date: Dec. 1, 2008

(87) PCT Pub. No.: WO2007/142569
PCT Pub. Date: Dec. 13, 2007

(65) Prior Publication Data
US 2009/0208369 A1    Aug. 20, 2009

(30) Foreign Application Priority Data
Jun. 2, 2006 (SE) ...................... 0601240

(51) Int. Cl.
*A61L 2/00* (2006.01)
(52) U.S. Cl. ............... 422/22; 422/23; 422/28; 53/425; 204/157.15
(58) Field of Classification Search ............. 422/22, 422/28, 37; 53/425; 204/157.15
See application file for complete search history.

(56) References Cited

U.S. PATENT DOCUMENTS

| 3,780,308 | A | * | 12/1973 | Nablo | 250/492.3 |
| 3,911,640 | A | | 10/1975 | Rausing | |
| 6,058,678 | A | | 5/2000 | Lees | |
| 6,221,216 | B1 | * | 4/2001 | Nablo et al. | 204/157.15 |
| 6,481,468 | B1 | * | 11/2002 | Taggart | 141/85 |
| 2001/0035500 | A1 | * | 11/2001 | Schianchi et al. | 250/455.11 |
| 2006/0067856 | A1 | | 3/2006 | Martensson et al. | |
| 2007/0253861 | A1 | * | 11/2007 | Naka et al. | 422/22 |

FOREIGN PATENT DOCUMENTS

| WO | WO 80/01457 A1 | 7/1980 |
| WO | WO 2004/054883 A1 | 7/2004 |

OTHER PUBLICATIONS

International Search Report (PCT/ISA/210), Oct. 9, 2007.

* cited by examiner

*Primary Examiner* — Sean E Conley
(74) *Attorney, Agent, or Firm* — Buchanan Ingersoll & Rooney PC

(57) ABSTRACT

A method of sterilizing a packaging material for, for example, a ready-to-fill package with extended shelf-life for a food involves bringing a sterilization agent containing hydrogen peroxide into contact with the packaging material in order to remove microorganisms present on the packaging material. After the contact with the sterilization agent, the packaging material is ventilated with air so as to remove remaining residues of hydrogen peroxide on and/or in the packaging material. The removal of the remaining residues of hydrogen peroxide is improved synergistically by exposing the packaging material, after contact with the sterilization agent but before ventilation, to accelerated electrons at a kinetic energy of at least 50 keV.

14 Claims, 1 Drawing Sheet

Figure 1:
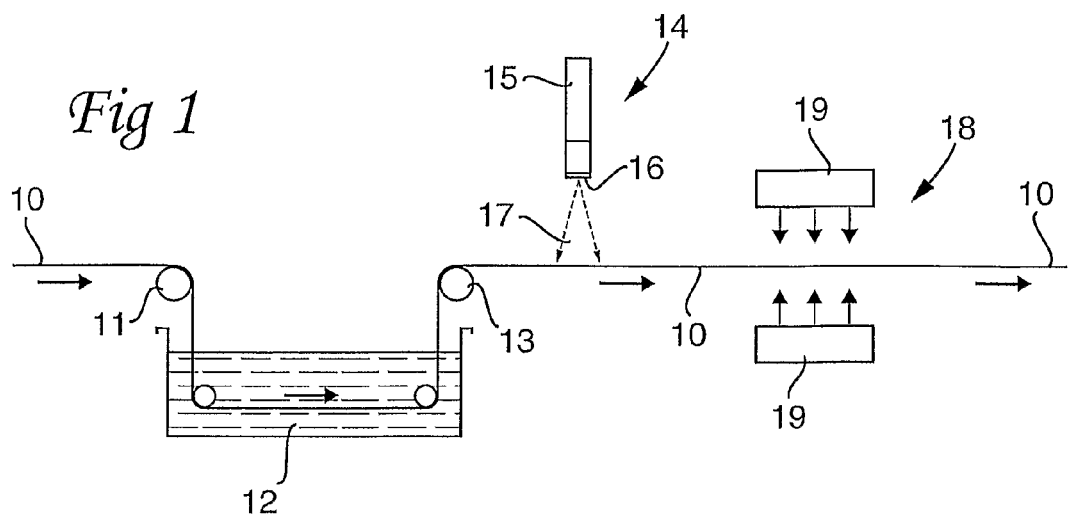

METHOD OF STERILIZING A PACKAGING MATERIAL BY MEANS OF A STERILIZATION AGENT CONTAINING HYDROGEN PEROXIDE

TECHNICAL FIELD

The present invention relates to a method of sterilizing a packaging material by means of a sterilization agent containing hydrogen peroxide, in which method the hydrogen peroxide-containing sterilization agent is brought into contact with the packaging material in order to eliminate microorganisms present on the packaging material, whereafter the packaging material is ventilated by means of air in order to remove remaining residual quantities of hydrogen peroxide on and/or in the packaging material.

BACKGROUND ART

Within the packaging technology, use is often made of a hydrogen peroxide-containing sterilization agent in order to sterilize a packaging material for a food so as to make for the storage of the food during extended shelf-lives or storage times without harmful effects on the quality properties of the food, such as flavour, aroma, colour and consistency. Depending upon the type which is to be packed, the requisite extermination or deactivation of microorganisms may vary from one type of food to another. For food types of the type which have a pH value of 4.6 or lower, e.g. juice and wine, the extermination need not be as extensive as for foods with higher pH values, e.g. milk, since a lower pH value per se counteracts the growth of surviving microorganisms during the storage time of the food. On the other hand, higher pH values have a weaker, or non-existent, inherent counteraction to such growth and, as a result, require a more extensive extermination of microorganisms in order to attain the desired extended shelf-life of the food.

The expression "sterilize" and equivalent variations of this expression are taken to signify sterilization levels ranging from practically total extermination of microorganisms to a more moderate sterilization level which may be sufficient to impart to foods with lower pH values (so-called high-acid foods) extended shelf-life.

According to a prior art sterilization method, packaging containers for a food with extended shelf-life are produced from a web of plastic-coated paper in that the web is, for purposes of sterilization, led through an aqueous bath of hydrogen peroxide (60-75° C.; approx. 35 weight %) during a sufficient stay-time in the bath in order to exterminate or deactivate microorganisms on the surface of the web.

After the passage through the hydrogen peroxide bath, remaining residual hydrogen peroxide is removed from the surface of the web by a combined mechanical and physical treatment of the web in connection with, or immediately after the exit of the web from the hydrogen peroxide bath.

The sterilized and treated web is reformed into a tube by both longitudinal edges of the web being united with one another in an overlap joint or seal, and the tube is filled with the pertinent food which has been sterilized separately by means of a suitable sterilization treatment prior to the filling operation. The tube is divided into continuous packaging units by repeated transverse sealing of the tube transversely of the longitudinal direction of the tube and below the filling level of the tube, at the same time as the packaging units are separated from one another by incisions in the transverse sealing zones. The separated packaging units are thereafter given the desired geometric configuration by a fold forming- and sealing operation. Known commercial examples of such aseptic packaging containers are TETRA BRIK®, TETRA CLASSIC® and TETRA PRISMA®

According to another prior art method, similar packaging containers are produced for a food with extended shelf-life from flat-folded tubular blanks of plastic-coated paper in that the blanks are first raised into open packaging cartons. The tubular packaging cartons are provided with a bottom closure by means of a fold forming- and sealing operation, whereafter the packaging cartons provided with a bottom are sterilized by means of gaseous or liquid hydrogen peroxide which is brought into contact with the inner walls of the packaging cartons in order to exterminate or deactivate any microorganisms present. After the contact with hydrogen peroxide, remaining residues of hydrogen peroxide are driven off physically, usually by means of air.

The sterilized packaging cartons are thereafter filled with a separately sterilized food and are finally provided with, a top closure, Known commercial examples of such packaging containers for foods with extended shelf-life are TETRA REX® and TETRA APTIVA®.

According to yet a further known method which is reminiscent of the immediately previously described method, plastic bottles are produced for foods with extended shelf-life, e.g. injection moulded PET bottles, in that the bottles, prior to filling, are sterilized by means of gaseous hydrogen peroxide which is injected into the bottles through the open bottle mouth for contact with the inner walls of the bottle. After contact with the hydrogen peroxide, the interior of the bottle is ventilated by means of air so as to drive off remaining residual quantities of hydrogen peroxide from the inner surfaces of the bottle.

The bottles are thereafter filled with the pertinent food and closed by means of, for example, a screw cap for further transport and handling.

A sterilization by means of hydrogen peroxide, as described above, most generally entails that the sterilized surfaces, in this case the inner walls of the sterilized packaging container and the bottle, respectively, display remaining residual quantities of hydrogen peroxide. Even if these residual quantities are normally extremely slight, most often 03 ppm or less, and have no harmful effect on the food, they nevertheless constitute an unnecessary consumption of hydrogen peroxide and thereby an unnecessary economic loss in the sterilization operation.

In order to reduce remaining residual quantities of hydrogen peroxide, it has previously been proposed in the art to combine such a chemical sterilization using hydrogen peroxide with a physical sterilization employing UV radiation, as described in, for example, WO-A-80/01457. As a result of this combination of chemical and physical sterilization, the concentration (and thereby the consumption) of hydrogen peroxide may be reduced to 10 weight % or even less, if the physical sterilization is carried out using a UV radiation within a wavelength range of below 325 nm.

Even if a combined chemical and physical sterilization using hydrogen peroxide and UV radiation thus implies that the consumed quantity of hydrogen peroxide may be reduced, at the same time as a synergistically improved sterilization effect may be achieved, it nevertheless does not fully resolve the problem involving remaining residual quantities of hydrogen peroxide. This is because, int. al., certain plastics in contact with aqueous hydrogen peroxide display a tendency to absorb the hydrogen peroxide which may therefore readily penetrate into and remain on and/or in such an absorbing plastic surface, for example the outer plastic coating of a packaging laminate. The depth of penetration of the hydrogen peroxide may in certain cases even be so great that the absorbed hydrogen peroxide is not accessible to, and therefore cannot be ventilated off using air. The penetration ability of the hydrogen peroxide into plastic may vary from one plastic to another, but is particularly serious in plastics of a hydrophilic nature, such as, for example, PET, in which it is readily absorbed and remains in position at relatively large penetration depths.

There is thus still a need to be able to reduce the consumed quantity of hydrogen peroxide in sterilization of packaging material by means of a sterilization agent containing hydrogen peroxide.

OBJECTS OF THE INVENTION

One object of the present invention is therefore to realise a method of sterilizing a packaging material by means of a hydrogen peroxide-containing sterilization agent of the type described by way of introduction by means of which consumed quantity of hydrogen peroxide can be reduced and can be maintained at a minimum.

A further object of the present invention is to realise a method of sterilizing a packaging material by means of a hydrogen peroxide-containing sterilization agent by means of which residual quantities of hydrogen peroxide on and/or in the packaging material may be reduced to a minimum, regardless of the material properties of the sterilized packaging material.

One particular object of the present invention is to realise a simple, but efficient method of sterilizing a web-shaped packaging material consisting wholly or partly of plastic, by means of a hydrogen peroxide-containing sterilization agent and by means of which residual hydrogen peroxide on and/or in the packaging material may be reduced to levels well below the prescribed levels, regardless of the plastic employed in the packaging material.

A further object of the present invention is to realise a method of sterilizing ready-to-fill packaging containers by means of a hydrogen peroxide-containing sterilization agent.

Still a further object of the present invention is to realise a method of sterilizing plastic bottles, e.g. PET bottles, by means of a hydrogen peroxide-containing sterilization agent with but insignificant or minimal quantities of residual hydrogen peroxide on and/or in the sterilized plastic surfaces.

These and also other objects of the present invention will be attained by means of a method which has the characterising features as disclosed in appended Claim 1.

Expedient embodiments of the method according to the present invention have further been given the characterising features as set forth in the appended subclaims.

BRIEF SUMMARY OF THE INVENTION

According to the present invention, there will thus be realised a method of sterilizing a packaging material, in which method a hydrogen peroxide-containing sterilization agent is brought into contact with the packaging material in order to eliminate microorganisms present on the packaging material, whereafter the packaging material is ventilated by means of air in order to remove remaining residual quantities of hydrogen peroxide on and/or in the packaging material. The method is characterised in that the sterilized packaging material, after the contact with the sterilization agent but prior to ventilation, is exposed to accelerated electrons with a kinetic energy of at least 50 keV.

According to the present invention, is has surprisingly proved that electron beams with a kinetic energy of at least 50 keV or radicals which are formed by collision between these electrons and hydrogen peroxide are sufficiently energetic to break down and remove residual hydrogen peroxide on and/or in the sterilized packaging material. In particular, it has proved that such electrons possess sufficient energy (as opposed, for example, to UV beams) in order also to be able to penetrate deep into the packaging material and collide with absorbed hydrogen peroxide which would otherwise have remained unaffected on and/or in the packaging material after the sterilization.

One surprising result which is attained by the method according to the present invention is thus a synergy combination effect of sufficiently energetic electron beams which, by collision, break down hydrogen peroxide, and radicals formed by the collision which per se may be sufficiently energetic to collide with and break down further hydrogen peroxide and thereby contribute to removing residual hydrogen peroxide on and/or in the packaging material. Since the radicals formed by collision do not necessarily move in the main direction of the colliding electrons but are rather scattered randomly in all directions from the point of collision, this implies that they may be scattered in directions transversely of the main direction of the electrons and thus also move "round corners" and reach into otherwise more or less inaccessible pockets and nooks at penetration depths below the surface of the packaging material.

According to the present invention, the electrons may have a kinetic energy within the range of 70-90 keV, which is sufficiently high to penetrate into the packaging material, but at the same time sufficiently low so as not to destroy the chemical structure in the packaging material. Since different plastics are sensitive to different levels to structural effect of electrons and certain plastics are, therefore, more sensitive than, others, according to the present invention electrons with a lower kinetic energy should therefore be used in connection with such more electron sensitive plastics (e.g. PE and PP) than for less electron sensitive plastics, e.g. PET. With the knowledge of the pertinent plastic, a person skilled in the art may therefore readily select a suitable level of kinetic energy for the electrons employed in the method according to the invention.

BRIEF DESCRIPTION OF THE ACCOMPANYING DRAWINGS

Figure 2:
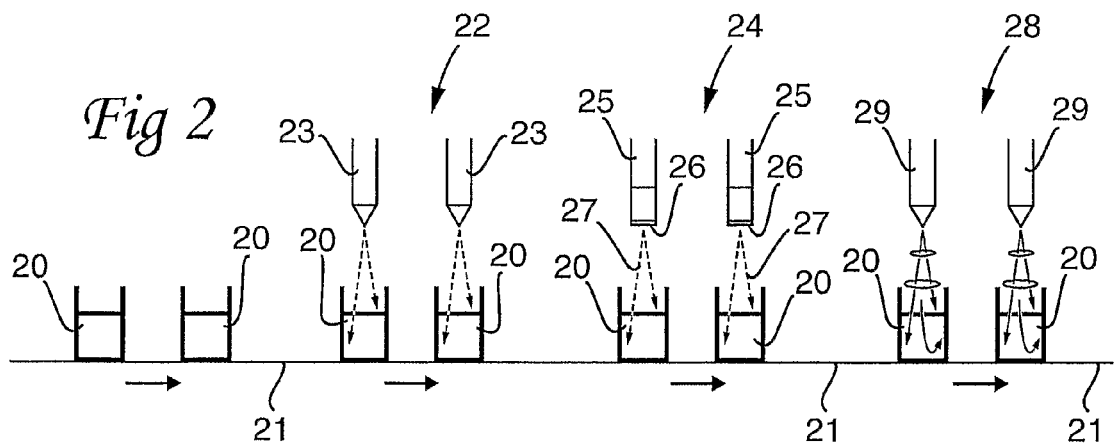
Figure 3:
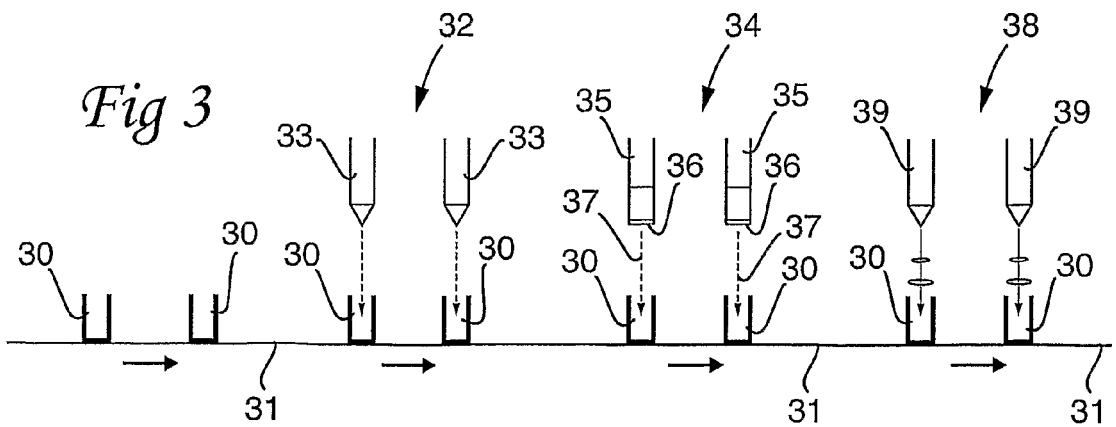

Further advantages and characterising features of the present invention will be described in greater detail hereinbelow, with reference to the accompanying Drawings. In the accompanying Drawings:

FIG. 1 schematically illustrates the sterilization of a web-shaped packaging material using the method according to the invention;

FIG. 2 schematically illustrates the sterilization of ready-to-fill packaging containers using the method according to the invention; and FIG. 3 schematically illustrates the sterilization of plastic bottles using the method according to the invention.

DETAILED DESCRIPTION OF THE INVENTION

It should be observed that the illustrated embodiments of the method according to the invention are merely intended to illuminate the invention and, therefore, should not be perceived as restrictive of the inventive concept as this is defined in the appended Claims.

FIG. 1 thus illustrates how a web 10 of a packaging material can be sterilized using the method according to the present invention. The web 10 is unwound from a magazine reel (not shown) which may, but need not necessarily be a magazine reel at the inlet end of a packing and filling machine of the type which, from the web, produces packaging containers for foods with extended shelf-life in accordance with the known form/fill/seal principle as described above. The web 10 is led in the direction of the arrow via a bending roller 11 down into, a bath 12 containing hydrogen peroxide at a concentration of approx. 35 weight % and a temperature of between 60 and 75° C., e.g. 65° C. for sufficiently lengthy contact with the hydrogen peroxide in the bath 12 so as to eliminate microorganisms present on the web 10.

The web 10 with remaining residual hydrogen peroxide on its surface is led up out of the bath and brought, in immediate association with the exit from the bath 12, into contact with a suitable mechanical means, e.g. a doctor blade urged against the surface of the web, or a press nip formed between two rollers, in order mechanically to remove entrained hydrogen peroxide from the surface of the web 10 and return this hydrogen peroxide down back into the bath 12 for renewed use.

From the mechanical means (not shown), the web 10 is thereafter led via a further bending roller 13 to an electron irradiation device carrying the generic reference numeral 14 so as to be irradiated with electrons with a view to removing further hydrogen peroxide from the sterilized web 10. In the illustrated example, the apparatus 14 includes an electron emitter 15 with a window 16 facing towards the surface of the passing web 10 from which a shower 17 of electron beams with a kinetic energy of at least 50 keV is continually directed towards the whole of the opposing surface of the web 10. The emitted electrons possess sufficient kinetic energy in order, on collision with hydrogen peroxide molecules on the surface of the web 10, to break them down and form radicals. The thus formed radicals are scattered in random directions in space and can in their turn, if they have sufficient longevity, collide with and break, down additional hydrogen peroxide which has not been impinged on by the primarily emitted electrons. By such means, there will be obtained a synergistic breakdown of residual hydrogen peroxide on the sterilized web 10, at the same time as the emitted electron beams per se are also sufficiently energetic to supplement and thereby elevate the sterilization effect of the hydrogen peroxide.

Even if emitted electrons with a kinetic energy of approx. 50-60 keV in most cases give a supplementary positive contribution to both the breakdown of residual quantities of hydrogen peroxide and to sterilization of the web 10, it may in certain cases be appropriate and even necessary to increase this kinetic energy up to approx. 70-90 keV in order to obtain the desired breakdown of residual hydrogen peroxide. This applies particularly in conjunction with packaging materials which include outer coatings of plastic which readily absorb hydrogen peroxide. One example of such a plastic is polyethylene terephthalate (PET) on which hydrogen peroxide not only remains on the surface but is also readily absorbed into the plastic down to a sufficiently great penetration depth so as not to be able to be reached by emitted electrons at insufficient kinetic energy. That kinetic energy which is to be employed may thus vary from case to case and is determined in each individual case by the composition of the packaging material, in particular the outer plastic coating. As a simple rule of thumb in the selection of kinetic energy, it however applies that the more inclined the relevant plastic coating is to absorb hydrogen peroxide, e.g. PET, the higher should be the level of kinetic energy which is selected, and correspondingly a lower level of kinetic energy is to be selected the lesser tendency of the pertinent plastic coating to absorb hydrogen peroxide, e.g. LDPE, HDPE and PP. Nevertheless, the kinetic energy must in every case be at least 50 keV in order to achieve the desired effect according to the present invention.

Occasionally, it may happen that the web 10 is provided with prepared opening devices with projecting parts, such as screw caps of plastic injection moulded direct on the web at regular spacing from one another corresponding to one package length. Such projecting parts may, to some degree, screen off subjacent portions of the web from the emitted electrons and thereby create concealed spaces where hydrogen peroxide may remain and may thus accompany the web unaffected. In order to minimise the risk of such accompanying, concealed hydrogen peroxide, it may, according to the present invention, be appropriate to mount the emitter 15 freely movable transversely over the entire width of the web in order thereby to be able to guide the emitted electron beams to all areas of the projecting parts, including the subjacent, concealed areas.

From the electron irradiation apparatus 14, the web 10 is thereafter led further to a ventilation apparatus 18 where the sterilized and irradiated web 10 is ventilated by means of air, preferably sterile air, which, with suitable means 19, 19 in communication with a source of air (not shown) is injected towards the web 10 in order to dry and drive off additional residues of hydrogen peroxide from the web 10.

The ventilated web 10 is thereafter led further for reforming into finished packaging containers for foods with extended shelf-life of the type described earlier, e.g. packaging containers of the following types: TETRA BRIK®, TETRA CLASSIC® and TETRA PRISMA®.

FIG. 2 schematically shows how open ready-to-fill packages 20 of a packaging material comprising outer coatings of plastic can be sterilized using the method according to the present invention. In such instance, the packages 20 are conveyed on an indexed moving conveyor belt 21 which conveys the packages in the direction of the arrow from an infeed end (to the left in the figure) to a sterilization apparatus carrying the generic reference numeral 22 for sterilization of the inner walls of the packages 20 by means of a hydrogen peroxide-containing sterilization agent. The sterilization agent may be either gaseous or liqueform and is injected through nozzles 23, 23 into the packages through the open end of the packages for contact with the whole of the inner surface of the packages.

From the sterilization apparatus 22, the sterilized packages 20 are thereafter conveyed to an electron irradiation apparatus carrying the generic reference numeral 24 where, in a corresponding manner, electron beams are brought into contact with all of the sterilized inner surfaces of the packages 20 in order to remove hydrogen peroxide from these surfaces. In the illustrated embodiment, the electron irradiation apparatus 24 includes two electron emitters 25, 25 which each have a window 26, 26 through which showers 27, 27 of accelerated electrons at a kinetic energy of at least 50 keV are aimed into the open packages 20.

The emitted electrons must have sufficient kinetic energy in order, on collision with hydrogen peroxide molecules on the inner surfaces of the packages 20, to break them down and form radicals. The thus formed radicals are scattered in random directions in space and can in their turn, if they have sufficient longevity, collide with and break down, additional hydrogen peroxide which has not been impinged on by the primarily emitted electrons. By such means, there will be attained according to the present invention a synergistic breakdown of residual hydrogen peroxide on the sterilized inner surfaces of the packages 20, at the same time as the emitted electron beams per se are also sufficiently energetic to supplement and thereby elevate the extermination effect of the hydrogen peroxide.

In the same manner as in the illustrated example in FIG. 1, the kinetic energy of the emitted electrons may vary and be selected in view of the material composition of the pertinent packaging material. If the packaging material has outer coatings of plastic of the type which readily absorb hydrogen peroxide, e.g. PET, there is thus selected a higher kinetic energy, e.g. within the range of between 70 and 90 keV, than in that case where the outer coatings of the packaging material consist of a plastic with a lesser tendency to absorb hydrogen peroxide, such as, for example, LDPE, HDPE and PP, where the selected kinetic energy may thus be lower, e.g. approx. 50 keV.

From the electron irradiation apparatus 24, the irradiated packages 20 are conveyed further to a ventilation apparatus 28 where residues of hydrogen peroxide inside the packages 20 and on the inner surfaces of the packages 20 is ventilated off by means of air, preferably sterile air which is injected into the packages 20 through nozzles 29, 29 in communication with a source of air (not shown).

From the ventilation apparatus 28, the packages 20 are conveyed to a filling station (not shown) where the packages are filled with sterilized food and are closed and sealed prior to further transport and handling of the packed food. Examples of packages for foods having extended shelf-life which may be produced in this manner are TETRA REX° and TETRA APTIVA®.

FIG. 3 finally schematically illustrates one example of how ready-to-fill bottles of PET may be sterilized using the method according to the present invention. In such instance, the bottles 30 are conveyed on an indexed moving conveyor belt 31 which conveys the bottles 30 in the direction of an arrow from an infeed end (to the left in the figure) to a sterilization apparatus carrying the generic reference numeral 32 for sterilization of the inner walls of the bottles 20 by means of a hydrogen peroxide-containing sterilization agent. The sterilization agent may be either gaseous or liqueform and is injected through nozzles 33, 33 into the bottles through the open mouth of the bottles for contact with the whole of the inner surface of the bottles 30.

From the sterilization apparatus 32, the sterilized bottles 30 are conveyed to an electron irradiation apparatus carrying the generic reference numeral 34 where electron beams are brought into contact with the sterilized inner surfaces of the bottles 30 so as to remove hydrogen peroxide from these surfaces. In the illustrated example, the electron irradiation apparatus 34 includes two electron emitters 35, 35 which each have a window 36, 36 through which showers 37, 37 of accelerated electrons at a kinetic energy of at least 50 keV are aimed into the bottles 30.

According to the invention, the emitted electrons must have sufficient kinetic energy in order, on collision with hydrogen peroxide molecules on the inner surfaces of the bottles 30, to break down these molecules and form radicals. The thus formed radicals are scattered in random directions in space and can, if they are sufficiently energetic and possess sufficient longevity, collide with and break down additional hydrogen peroxide which has not been impinged on by the primarily emitted electrons. By such means, there will be attained according to the present invention a synergistic breakdown of residual hydrogen peroxide on the sterilized inner surfaces of the bottles 30, at the same time as the emitted electron beams per se are also sufficiently energetic to supplement and thereby elevate the extermination effect of the hydrogen peroxide.

Since the bottles 30 in the illustrated example consist of a plastic (PET) which readily absorbs hydrogen peroxide to penetration depth at levels which lie below the levels which can be reached by electron beams at a kinetic energy of only approx. 50 keV, the emitted electrons in this case are given greater kinetic energy, e.g. 70-90 keV, which is sufficient for the electrons to penetrate into and collide with the absorbed hydrogen peroxide also at these deeper levels.

From the electron irradiation apparatus 34, the bottles 30 are led further on the conveyor belt 31 to a ventilation apparatus carrying the generic reference numeral 38 where residues of hydrogen peroxide inside the bottles 30 and on the inner surfaces of the bottles 30 are ventilated off by means of air, preferably sterile air, which is injected into the bottles 30 through nozzles 39, 39 in communication with a source of air (not shown).

After the ventilation apparatus 38, the sterilized and ventilated PET bottles 30 are ready to be filled with a food at a filling station (not shown) where the bottles 30 are filled with sterilized food and closed by means of, for example, a screw cap or similar closure device for further transport and handling.

INDUSTRIAL APPLICATION

The method according to the present invention may be used in connection with a filling machine of the type which, from a web or from prefabricated blanks of a packaging material, produce so-called aseptic packages or packages with extended shelf-life for foods. In particular, the method according to the present invention may be employed in connection with a filling machine for blow moulded PET bottles which, prior to filling, are to be sterilised by means of a sterilization agent containing hydrogen peroxide.

What is claimed is:

1. The method of sterilizing a packaging material comprising: bringing a sterilization agent containing hydrogen peroxide into contact with the packaging material to remove microorganisms present on the packaging material; ventilating the packaging material, after contact with the sterilization agent, by air to drive off residual quantities of hydrogen peroxide from the sterilized packaging material; and exposing the sterilized packaging material, after contact with the sterilization agent but before the ventilation, to accelerated electrons at a kinetic energy of at least 50 keV, wherein the packaging material comprises outer coatings of a plastic which is selected from among polyethylene and polypropylene; and wherein the exposing of the packaging material to accelerated electrons comprises irradiating a web-shaped packaging material with the accelerated electrons.

2. The method of sterilizing a packaging material comprising: bringing a sterilization agent containing hydrogen peroxide into contact with the packaging material to remove microorganisms present on the packaging material; ventilating the packaging material, after contact with the sterilization agent, by air to drive off residual quantities of hydrogen peroxide from the sterilized packaging material; and exposing the sterilized packaging material, after contact with the sterilization agent but before the ventilation, to accelerated electrons at a kinetic energy of at least 50 keV, wherein the packaging material is an open ready-to-fill package, and the exposing of the packaging material to accelerated electrons comprises exposing all inner surfaces of the open, ready-to-fill package, after contact with the sterilization agent but before ventilation with air, to the accelerated electrons.

3. The method as claimed in claim 2, wherein the packaging material displays outer coatings of a plastic which has been selected from among polyethylene and polypropylene; and the exposure of all the inner surfaces of the package to accelerated electrons comprises exposing all of the inner surfaces of the package to accelerated electrons at a kinetic energy of approx. 50-70 keV.

4. The method as claimed in claim 2, wherein the open ready-to-fill package is a blow-molded ready-to-fill bottle of PET, and the exposing of the packaging material to accelerated electrons comprises exposing all inner surfaces of the bottle, after contact with sterilization agent but before the ventilation, to accelerated electrons at a kinetic energy of 70-90 keV.

5. A method of sterilizing a ready-to-fill package, having an open end communicating with an interior of the package, to be used in packaging food products, the method comprising:
contacting all inner surfaces on the interior of the package with a hydrogen peroxide-containing sterilization agent to remove microorganisms on the inner surfaces;
directing accelerated electrons having a kinetic energy of at least 50 keV into contact with the inner surfaces on the interior of the package, after contacting all the inner surfaces on the interior of the package with the hydrogen peroxide-containing sterilization agent, so that the accelerated electrons collide with the hydrogen peroxide to break down the hydrogen peroxide; and
ventilating the interior of the package with air, after contacting the inner surfaces on the interior of the package with the accelerated electrons, to remove residual quantities of the hydrogen peroxide from the inner surfaces of the package.

6. The method as claimed in claim 5, wherein the directing of the accelerated electrons at the inner surfaces on the interior of the package comprises contacting all of the inner surfaces of the package with the accelerated electrons.

7. The method as claimed in claim 5, wherein the package is a packaging container made of packaging material that includes an outer coating comprised of at least one of polyethylene plastic and polypropylene plastic; and the directing of the accelerated electrons into contact with the inner surfaces on the interior of the package comprises directing accelerated electrons at a kinetic energy of approx. 50-70 keV into contact with all of the inner surfaces on the interior of the packaging container.

8. The method as claimed in claim 5, wherein the package is a blow-molded ready-to-fill PET bottle, and the directing of the accelerated electrons into contact with the inner surfaces on the interior of the package comprises directing accelerated electrons at a kinetic energy of 70-90 keV into contact with all of the inner surfaces on the interior of the PET bottle.

9. A method of sterilizing a longitudinally extending web of packaging material used to produce ready-to-fill packages for packaging food products, the method comprising:
contacting all surfaces of the longitudinally extending web of packaging material with a hydrogen peroxide-containing sterilization agent to remove microorganisms on the web of packaging material;
directing accelerated electrons having a kinetic energy of at least 50 keV into contact with the surfaces of the web of packaging material, after contacting all the surfaces of the web with the hydrogen peroxide-containing sterilization agent, so that the accelerated electrons collide with the hydrogen peroxide to break down the hydrogen peroxide; and
directing air at the surfaces of the web of packaging material, after directing the accelerated electrons at all surfaces of the web of packaging material, to remove residual quantities of the hydrogen peroxide from the surfaces of the web of packaging material.

10. The method as claimed in claim 9, wherein the directing of the accelerated electrons into contact with the surfaces of the web of packaging material comprises contacting all of the surfaces of the web of packaging material with the accelerated electrons.

11. The method as claimed in claim 9, wherein the directing of the accelerated electrons into contact with the surfaces of the web of packaging material comprises directing accelerated electrons at a kinetic energy of 50-60 keV into contact with the surfaces of the web of packaging material.

12. The method as claimed in claim 9, wherein the web is provided with prepared opening devices with projecting parts, and the accelerated electrons are directed into contact with the surfaces of the web of packaging material by an emitter which is movable over a width of the web.

13. The method as claimed in claim 9, wherein the contacting of all of the surfaces of the longitudinally extending web of packaging material with the hydrogen peroxide-containing sterilization agent comprises conveying the web of packaging material through a bath containing hydrogen peroxide so that a portion of the web of packaging material is immersed in the bath containing the hydrogen peroxide.

14. The method as claimed in claim 1, wherein the web-shaped packaging material is irradiated with the accelerated electrons at a kinetic energy of 50-60 keV.

* * * * *